US006461809B1

(12) United States Patent
Hallowitz et al.

(10) Patent No.: US 6,461,809 B1
(45) Date of Patent: *Oct. 8, 2002

(54) METHODS OF IMPROVING INFECTIVITY OF CELLS FOR VIRUSES

(75) Inventors: Robert A. Hallowitz, Gaithersburg, MD (US); Susan Young, Albuquerque, NM (US); Chester King, Frederick, MD (US)

(73) Assignee: Bio-Tech Imaging, INC, Frederick, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/299,625

(22) Filed: Apr. 27, 1999

(Under 37 CFR 1.47)

Related U.S. Application Data

(63) Continuation of application No. 09/139,663, filed as application No. PCT/US97/18649 on Oct. 15, 1997, which is a continuation-in-part of application No. 08/732,782, filed on Oct. 15, 1996, now Pat. No. 5,817,458, and a continuation-in-part of application No. 08/732,784, filed on Oct. 15, 1996, now Pat. No. 5,714,390.

(60) Provisional application No. 60/083,078, filed on Apr. 27, 1998.

(51) Int. Cl.$^7$ .............................. C12Q 1/70; C12Q 1/00; G01N 33/53

(52) U.S. Cl. .................... 435/5; 435/3; 435/4; 435/7.1; 435/7.2; 435/7.23; 435/7.24; 435/7.92; 436/512; 436/513; 436/518; 436/525; 436/526

(58) Field of Search ............................ 435/5, 3, 4, 7.1, 435/7.2, 7.23, 7.24, 7.92; 436/512, 513, 518, 525, 526

(56) References Cited

U.S. PATENT DOCUMENTS 4,659,678 A * 4/1987 Forrest et al. .............. 436/512
5,256,532 A * 10/1993 Malnicoff et al. ............. 435/5

FOREIGN PATENT DOCUMENTS

| WO | 97/28258 | 1/1997 |
| WO | 98/00535 | 6/1997 |
| WO | 99/67429 | 6/1999 |

OTHER PUBLICATIONS

Chacherian et al.; Human Immunodeficiency Virus Type 1 Coreceptors Participate in Postentry Stages in the Virus Replication Cycle and Function in the Simian Immunodificency Virus Infection; Journal of Virology; vol. 71, No. 5; pp. 3932–3939, May 1997.*

Deng et al.; Identification of a Major Co–receptor for Primary Isolates of HIV–1; Nature; vol. 381; pp. 661–666, Jun. 1996.*

B. Chackerian et al., *Journal of Virology*, vol. 71, No. 5, pp. 3932–3939 (1997).

Paul R. Clapham et al., *Nature*, vol. 388, pp. 230–231 (1997).

* cited by examiner

*Primary Examiner*—Hankyel T. Park
*Assistant Examiner*—Stacy S. Brown
(74) *Attorney, Agent, or Firm*—Millen, White, Zelano & Branigan, P.C.

(57) ABSTRACT

The present invention relates to cells which have improved receptivity to viruses which are capable of infecting them. Receptivity to such viruses is improved by selecting cells from a population which express the receptor(s) that enable a virus to attach to the cell and gain entry into it. Any combination of viruses and host cell lines can be used. In a preferred embodiment, the present invention relates to improving receptivity or infectivity of a cell line which can be infected with an immunodeficiency virus, such as HIV-1. Especially preferred embodiments of the invention relate to methods of improving (or assaying for) the infectivity for HIV-1 in a HIV-1 receptive cell line, preferably a continuous cell line transformed with DNAs coding for expressible CD4 and expressible HIV-1 coreceptor, comprising, in any effective order, a) isolating the cells expressing CD4 and an HIV-1 coreceptor on their cell surface; b) contacting the isolated cells with HIV-1 under conditions effective for the HIV-1 to infect the cells; and c) detecting the number of cells infected with HIV-1, thereby assaying for infectivity of HIV-1. This method facilitates the measurement of true infectivity and infectivity reduction values by quantifying the percentage of infected cells in the population of specific cells capable of being infected by virus, rather than in a population of mixed cells, only some which are capable of being infected.

18 Claims, 2 Drawing Sheets

METHODS OF IMPROVING INFECTIVITY OF CELLS FOR VIRUSES

CROSS REFERENCE TO RELATED APPLICATIONS

This application claims the benefit of the filing date on U.S. Provisional Application Ser. No. 60/083,078, filed Apr. 27, 1998.

This application is a continuation of Ser. No. 09/139,663 filed Aug. 25, 1998 which is a 371 of PCT/US97/18649, filed Oct. 15, 1997, which is a continuation-in-part of U.S. Ser. No. 08/732,782, filed Oct. 15, 1996, now U.S. Pat. No. 5,817,458, and U.S. Ser. No. 08/732,784, filed Oct. 15, 1996, now U.S. Pat. No. 5,714,390, all of which are incorporated by reference herein.

BACKGROUND OF THE INVENTION

There is historical precedent for the use of flow cytometry to identify and quantitate HIV-infected cells. Investigators in the late eighties and early nineties demonstrated flow cytometry's ability to identify and quantitate HIV-1 infected mononuclear cells at low frequency in lymphoid cell lines and whole blood.

The means of identification used at first, however, was to treat HIV- infected cells, derived from human T lymphoid cell lines H9 and A3.01, with an HIV- inactivating, permeabilizing fixative. This was followed by binding with a monoclonal antibody specific for the major core protein p24, and then by binding with FITC-conjugated $F(ab')_2$ fragments of goat anti-mouse immunoglobulin antibody (Cory, J. M., et al. 1987). The method allowed determination of the percentage of the cell population that was infected and the relative amount of p24 antigen per cell. The first of such work utilized the T-cell adapted strain HIV in H-9 cells, and was able to detect as few as 1 HIV-1 infected cell in 10,000.

Shortly thereafter, a number of workers studied HIV-1 infected mononuclear cells using staining procedures for intracellular p24, and flow cytometric analysis of peripheral blood from seropositive patients throughout the spectrum of HIV disease progression. Using Centers for Disease Control (CDC) criteria, they were able to demonstrate that HIV-1 infected peripheral blood mononuclear cells (PBMCs) could be separated from whole blood. This was done by utilizing fixation and permeabilization and/or live cell immunofluorescence to gain entry to the core protein p24 with monoclonal anti-p24 antibodies. FITC labeling was accomplished with a goat/human anti-globulin conjugate. Flow cytometric analysis revealed clear and statistically significant differences in quantities of HIV-1 infected PBMCs between seropositive patients in CDC Classes I, II, and III, but not between patients in Classes III and IV.

The percent of HIV-1 infected PBMCs in seropositive individuals, when detectable, ranged form 4% to as high as 25%, while seronegative controls never exceeded 0.1% (autofluorescence). The consensus from several authors was that there was a correlation between the fall in CD4 counts and the sharp increase in PBMC virus loading. Thus flow cytometry, used to quantitate PBMCs productively or latently infected by HIV-1, has been recognized as a valuable tool. This tool can be used most effectively to further the understanding of various pathogenic aspects of the disease, better define the stages of the disease, and enhance the capacity to tailor therapeutic strategies.

Comparisons of both the technical and rather large percentage differences reported by different authors in various studies highlight the limitations of PCR as a means to label HIV-infected cells. A current limitation of PCR used on extracted DNA is the difficulty in correlating the presence of the viral genome with a single cell, and thus determine the exact percentage of HIV-1-producing cells.

On the other hand, in situ hybridization procedures suffer from low sensitivity. Although they are capable of identifying the single infected cell, these procedures are further compromised by requiring the microscopic screening of a large number of cells to determine the exact percentage of HIV-1 infected mononuclear cells in peripheral blood utilized the product of and in situ PCR assay to demonstrate the presence of proviral DNA.

Determination of the efficacy of vaccine candidates for the treatment and/or prevention of HIV disease relies on the ability of the candidate agent to substantially reduce HIV reproduction. This is true also for passive immunotherapeutic agents (engineered neutralizing monoclonal and polyclonal antibodies). Within the past few years, it has become clear that primary HIV-1 isolates, while relatively resistant to neutralization by antibodies as well as by CD4-based reagents, can be strongly neutralized by certain monoclonal antibodies (mAbs) and by some sera from HIV-1 infected people.

Primate retroviruses, such as HIV-1 and simian immunodeficiency virus (SIV), share a primary cellular receptor, the CD4 molecule. Isolates of HIV-1 have been generally characterized on the basis of their replication patterns in peripheral blood mononuclear cells (PBMCs), primary macrophages, and immortalized T-cell lines. All HIV-1 isolates are able to replicate to some degree in PBMC cultures; M-tropic viruses also replicate in macrophages, but T-tropic viruses replicate in T cell lines, and dual tropic viruses replicate in all three types of cells.

Additional (secondary) determinants for HIV-1 fusion and entry have recently been identified on the basis of their interactions with chemokines called macrophage inflammatory protein $1\alpha$ (MIP-$1\alpha$), MIP-$1\beta$, and RANTES, which act as powerful modulators of HIV-1 infection. T- and M-tropic isolates have been shown to require the chemokine receptors CXCR4 (fusin) and CCR5 as the major HIV-1 coreceptors respectively. The above-named chemokines have been shown to block M-tropic HIV1 strains because they are competitive ligands for the CCR5 receptor.

The key to performing a highly sensitive, accurate, and consistent neutralization assay depends upon the assay conditions used. These may include: the type and strain of virus used, the multiplicity of infection, the ratio of antibody to virus, the length of exposure of the antibody-treated virus to target cells, the type of target cell used for infection, the kinetics of virus growth, the length of the assay, the type of read-out used, the method of data analysis, and the criteria used to define neutralization. The neutralization and the infectivity reduction assays remain in a paradoxically underdeveloped state, in spite of increased efforts to develop new neutralizing agents. It is not surprising, therefore, that studies of HIV-1 neutralization have shown significant differences in results because of dependence on many of the variables listed above, for which there are no uniformly accepted standards.

DESCRIPTION OF THE INVENTION

The present invention relates to cells which have improved receptivity to infecting viruses. Receptivity to such viruses is improved by selecting cells from a population which express the receptor(s) that enable a virus to attach to the cell and gain entry into it. Any combination of viruses and host cell lines can be used in the present invention.

In a preferred embodiment, the present invention relates to improving receptivity or infectivity of a cell line which can be infected with an immunodeficiency virus, such as HIV-1. Especially preferred embodiments of the invention relate to methods of improving (or assaying for) the infectivity for HIV-1 in a HIV-1 receptive cell line, preferably a continuous cell line transformed with DNAs coding for expressible CD4 and expressible HIV-1 coreceptor, comprising, in any effective order, a) isolating the cells expressing CD4 and an HIV-1 coreceptor on their cell surface; b) contacting the isolated cells with HIV-1 under conditions effective for the HIV-1 to infect the cells; and c) detecting the number of cells infected with HIV-1, thereby assaying for infectivity of HIV-1. This method facilitates the measurement of true infectivity and infectivity reduction values by quantifying the percentage of infected cells capable of being infected by virus, rather than in a population of mixed heterogenous cells, only some which are capable of being infected. Cells which have been selected for improved receptivity in accordance with the present invention are treated in a manner such that they remain viable and continue to be receptive to viral infection, i.e., the cells are not treated with a fixative such as formaldehyde or subjected to other conditions which impair their ability to be utilized in assays which require viral receptivity.

Infectivity of HIV-1 can be measured in any desired population of cells, including established primary cells, cell lines, and genetically-engineered cells, etc., which are receptive for HIV-1. By the phrase, "receptive for HIV-1," it is meant that the cells are capable of being infected by HIV-1. For example, it is known that the phenotypic marker and HIV receptor CD4 and certain HIV-1 coreceptors, such as CCR5 or CXCR4 (fusin) and other coreceptors as mentioned below, are utilized by HIV-1 to enter a cell and effect productive infection. Receptive cells would possess one or more of these receptors on their cell surface. The receptors can be normally present on cells, can be introduced by genetic-engineering, or a combination thereof.

Primary cells for use in the present invention can be obtained from any desired source. For instance, cells can be isolated from a host, including: peripheral blood mononuclear cells; lymphocytes, such as T-cells (CD4, CD8, cytolytic, helper), B-cells, natural killer cells; mononuclear phagocytes, such as monocytes, macrophages, epithelioid cells, giant cells, microglia, Kupffer cells, alveolar macrophages; dendritic cells, such as interdigitating dendritic cells, Langerhans cells, or follicular dendritic cells; granulocytes; CD4-bearing cells; fibroblasts; cells obtained from generative organs, peripheral organs, bone marrow, thymus, lymph nodes, adenoids, spleen, Peyer's patches in the lamina propria of small intestine, tonsils in the pharynx, submucousal lymphoid follicles in the appendix and upper airways; peripheral blood; brain; peripheral and the central nervous system; cells from host infected with HIV-1; cells from hosts uninfected with HIV-1.

Any cell lines which are receptive for HIV-1 can be used. Preferred cell lines are "continuous cell lines," cells which can be maintained in culture, e.g., immortalized cells, transformed cells, cells adapted to cell culture, tumor cells, etc. Useful continuous cell lines include those listed in the ATCC Catalog of Cell Lines and Hybridomas. Preferred cell lines are mammalian cells, such as human cells, e.g., HeLa or lymphoblastoid cells.

In certain embodiments of the present invention, infectivity is measured in engineered cells, e.g., genetically-engineered cells into which exogenous nucleic acid has been introduced and/or expressed. The cells are preferably engineered to express one or more coreceptors for HIV-1, conferring and/or enhancing HIV-1 receptivity on such cells. By introducing and expressing nucleic acid coding for CD4 and/or the coreceptors into cells which normally do not express these proteins, receptivity can be conferred on the engineered cells. Other genetic techniques can also be used to introduce receptors or coreceptors for HIV-1 into cells, including cell fusion, oncogenic transformation, etc.

For instance, a continuous cell line transformed with nucleic acid coding for expressible CD4 and expressible HIV-1 coreceptor can be used as a receptive cell line. By the term "expressible," it is meant that the nucleic acid comprises sequences that facilitate production of desired polypeptide in the cell. For instance, a coding sequence for the HIV receptor, CD4, or, an HIV-1 coreceptor, etc., can be expressible in the sense that it is operably linked to an expression control sequence. The phrase "expression control sequence" means a nucleic acid sequence which regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, cell-type specific elements, or sequences which allow selective or specific cell expression etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can be heterologous or endogenous to the normal gene. Expression control sequences can be selected for host cell compatibility and a desired purpose, e.g., high copy number, high amounts, induction, amplification, controlled expression. Introduction, selection, and use of these sequences can be accomplished routinely, in accordance with methods that are well known in the art.

A nucleic acid can be introduced into the cell by any effective method including, e.g., naked DNA or RNA, Polybrene, calcium phosphate precipitation, electroporation, injection, DEAE-dextran-mediated transfection, fusion with liposomes, associated with agents which enhance its uptake into cells, viral transfection. A cell into which a nucleic acid has been introduced can be referred to as a transformed host cell. The nucleic acid can be extrachromosomal or integrated into a chromosome(s) of the host cell. Cells can be stably transformed or transiently transformed by any suitable method. See, for example, Ausubel, et al., "Introduction of DNA Into Mammalian Cells," in *Current Protocols in Molecular Biology*, sections 9.5.1–9.5.6 (John Wiley & Sons, Inc. 1995). Cells can also be engineered as described in Chackerian et al., *J. Virol.*, 71:3932–3939, 1997.

When a cell line has been transformed with nucleic acid it can be cultured under suitable conditions to express the nucleic acid. These conditions can be routinely selected, e.g., whether the sequences are constitutive, inducible, etc. Effective conditions includes any culture conditions which are suitable for achieving production of the polypeptide by the host cell, including effective temperatures, pH, medias, additives to the media in which the host cell is cultured (e.g., additives which amplify or induce expression such as butyrate, or methotrexate if the coding nucleic acid is adjacent to a dhfr gene), cyclohexamide, cell densities, culture dishes, etc.

Nucleic acid coding for HIV-1 coreceptors, and other sequences useful to facilitate or enhance receptivity, can be obtained routinely. Examples of coreceptors include: CCR5, CXCR4, CCR3, CCR2b, Bonzo, STRL33, BOB, GPR15, GPR1, US28. See, e.g., Nature, 388:230–231, 1997; J. Virol., 71:1657–1661, 1997; Dean et al., Science, 273:1856–1862, 1996; E. A. Berger, 1997, AIDS, 11:S3–S16; Broder et al., 1997, J. Leukocyte Biol., 62:20–29; Doms et al., 1997, Virology, 235:279-190; and Moore et al., 1997, Curr. Opinion Immunol., 9:551–562.

A cell line can be engineered to express one or more of these coreceptors. For instance, it is known that the differential utilization of CCR5 and CXCR4 by HIV strains explains differences in viral infectivity at the level of viral entry into the cell. CCR5 supports infection by R5 (M-tropic) virus strains, while CXCR4 supports infection by X4 (T-tropic) virus isolates. Alkhatib et al., 1996, Science, 272:1955–1958; Berger et al., 1998, Nature, 391:240; Choe et al., 1996, Cell, 85:1135–1148; Deng et al., 1996, Nature, 381:661–666; Doranz et al., 1996, Cell, 85:1149–1158; Dragic et al., 1996, Nature, 381:667–673; and Feng et al., 1996, Science, 272:872–877). R5-X4 (dual-tropic) viral env proteins can, in conjunction with CD4, use either CCR5 or CXCR4 for cellular entry. Thus, the choice of coreceptor can depend upon the virus which is to be assayed for infectivity. A cell line expressing multiple coreceptors can be utilized to measure infectivity of a wide range of different viruses which use different coreceptors.

Useful cell lines include, but are not limited to, e.g., HeLa-CD4-LTR-β-gal (MAGI); MAGI-CCR-5; S-MAGI (CCR5 or CXCR4). See, e.g., Chackerian et al., J. Virol., 71:3932–3939, 1997. In addition, PMBC's (and subpopulations thereof), T cell lines, lymphoblastoid cell lines, H9, C8166, Molt, Molt-4, CEM, Jurkat, preferably, CEMX174, HUT 78, U87.CD4. See, e.g., Virology, 236:208–212, 1997.

As explained above, the infectivity assays in accordance with the invention involve isolating the cells expressing CD4 and one or more HIV-1 coreceptors on their cell surface for use in assays for measuring or improving infectivity. The term "improving" has its normal meaning, i.e., to increase, to make better, etc., the efficiency of a particular cell line in becoming infected with a virus. As explained above, efficacy of particular viral strains has been underestimated since investigators failed to consider that not all the cells in a challenged population actually expressed the coreceptors on the cell surface. By enriching the population for cells which actually co-express the receptors necessary for virus entry into the cell, the infectivity of the population is improved in comparison to populations which have not been screened for the presence of such receptors.

The term "isolating," has its ordinary meaning, e.g., separating, separating out, setting apart, to select from among others, obtaining from or resulting from selection or separation. Generally, a starting population of cells to be challenged with virus can comprise both cells receptive for HIV-1, e.g., expressing both CD4 and a coreceptor simultaneously on the cell surface and cells which express only one of the viral receptors and which therefore can not be efficiently infected with virus. A function of this step is to obtain those cells which express both receptors on their cell surface, enriching the population in HIV-1 receptive cells. Isolating these cells can be accomplished in any suitable manner. In the examples below, preferred embodiments are described where cells are sequentially separated from others using immunomagnetic separation, by first obtaining cells which express CD4, and then selecting for cells among them which also express a HIV-1 coreceptor. However, the present invention is not limited to these examples as other methods and techniques which accomplish the same can also be utilized, e.g., FACS, cell-sorting, panning techniques using binding reagents attached to solid phases, etc.

In the preferred embodiments of the invention, the isolating is accomplished by first labeling cells expressing the viral receptors on their cell surface and then capturing the labeled cells. Labeling can be accomplished using any suitable "binding reagent," i.e., any agent which recognizes the viral receptor, e.g., antibodies (monoclonal, polyclonal, chimeric, single-chain, divalent, disulfide-stabilized Fv fragments, etc.), peptides, small molecules, cytokines, ligands, etc. For example, a "CD4 binding reagent" can be an antibody which is specific for CD4 (see below), soluble gp120, or MHC Class II binding ligands. Similar, a "HIV-1 coreceptor binding reagent" can be an antibody specific for a coreceptor or its natural ligand.

In the preferred embodiments of the invention, the labeling and separating is accomplished by immunomagnetic separation. For instance, a method of the invention involves: contacting said cells with a viral receptor first binding reagent under conditions effective for the binding reagent to label cell-surface viral receptor; contacting the cell-surface labeled cells with a second binding reagent attached to a magnetic particle, where the second binding reagent can attach or bind to the first binding reagent when on the cell-surface; applying a magnetic field to said labeled cells which is effective to retain said magnetic particles; and eluting the retained particles to form a sample of separated cells.

The first binding reagents in accordance with preferred methods are antibodies, including both monoclonal, polyclonal, and engineered antibodies. For instance, preferred antibodies are a CD4-specific antibody and a CCR-5 specific antibody. The term "specific" has its art-recognized meaning, e.g., an antibody obtained from a response that has been elicited by CD4, or a fragment thereof; antibodies are able to distinguish between subtle differences antigens—an antibody which is "specific" for CD4 can distinguish this antigen from different antigens having different specificities. Antibodies can be obtained commercially or prepared according to conventional methods. See, e.g., screening recombinant immunoglobulin libraries (Orlandi et al., Proc. Natl. Acad. Sci., 86: 3833–3837, 1989; Huse et al., Science, 256: 1275–1281, 1989); in vitro stimulation of lymphocyte populations; Winter and Milstein, Nature, 349: 293–299, 1991. For example, viral receptors can be administered to mice, goats, or rabbit subcutaneously and/or intraperitoneally, with or without adjuvant, in an amount effective to elicit an immune response. The antibodies can also be single chain or FAb fragments. The antibodies can be IgG, subtypes, IgG2a, IgG1, etc. Antibodies, and immune responses, can also be generated by administering naked DNA See, e.g., U.S. Pat. Nos. 5,703,055; 5,589,466; 5,580, 859. See, also, Harlow and Lane, Antibodies: A Laboratory Manual, Cold Spring Harbor Laboratory, 1988; Goding;

*Monoclonal Antibodies: Principles and Practice*, 2$^{nd}$ Ed. Academic Press N.Y., 1986.

Once cells have been assayed and their receptivity improved, they can be used in any method, technique, process, etc., which uses receptive cells. For instance, as mentioned above, receptive cell lines are useful in neutralization and infectivity reduction assays, drug screening assays, e.g., for measuring the effects of immunotherapeutic agents and other agents which block HIV-1. They can also be useful in cytokine production and in signal transduction assays. In general, these cells are useful in screening for any viral agent for which the binding protein(s) or receptor(s) are known. Assays can be carried out according to any suitable method, e.g., Zhang et al., Virology, 244: 430–41, 1998.

DETAILED DESCRIPTION OF THE INVENTION

In order to develop a more sensitive, accurate and reproducible method to assess neutralization for HIV-1 primary isolates, the MAGI-CCR5 cell line was chosen because of its proven receptivity to M-tropic, T-tropic, and dual tropic strains. In setting up our neutralization experiments, some fundamental deficiencies were notice in the development of past neutralization assay protocols for evaluating both efficacy of neutralizing antibodies and the infectivity of primary isolates. An important aspect is the receptivity of the cell line. It has been assumed that a specific cell line in culture has uniform receptivity based upon its general infrastructure. However, it was found that the percentage of cells expressing the receptors in question must be established in the beginning, and then how many of the receptors are expressed on each receptor-bearing cell should be determined. If this is not done, there will be a situation where the variable receptor expression will alter the target cell's receptivity to the virus, and the target cell's actual function might be read as an isolate or a neutralizing antibody.

When MAGI CCR5 cultures were inoculated at 30–50% confluence, it was assumed there was a high percentage of both CD4 and CCR5 expression. When, however, very low infectivity was found on day three, it was assumed that there was some mistake made during the process. What was discovered was that, out of the CD4 receptor cells in the culture, only 13% of them were expressing CD4, while 85% of them were expressing CCR5. Therefor, the limiting factor of infectivity was the lack of CD4-expressing cells. When actually measured, the percentage of essential receptor-bearing cells may actually be below 20% and can be as low as 5%. This is even though MAGI-CCR5 cells are expected to have a high rate of CD4 and CCR5 expression. Such a lack of receptor expression clearly distorts the infectivity quantitation of the primary isolate under consideration.

The current invention demonstrates a method by which a standard is created for optimizing target cell receptively and then, using flow cytometry, measuring HIV-1 primary isolate infectivity. Target cell receptivity is optimized in this invention by the positive selection of the CD4- and CCR5-expressing cells. Using immunomagnetic separation and the re-culturing of these cells, a minimum concentration of 85% receptor bearing cells (both CD4 and CCR5) prior to inoculation with the viral isolate is achieved.

Advantages of the present invention include:
1. Accurately determine the actual number of receptor-bearing cells in a population;
2. Accurately determine the number of receptor molecules on each receptor-bearing cell;
3. Concentrate the population of receptor-bearing cells to values approaching 100% of each receptor required for viral binding/fusion;
4. Monitor the consistency of each receptor's expression post-inoculation;
5. Establish true infectivity and infectivity reduction values by quantifying the actual percentage of infected cells from the population of receptor-bearing cells, in which the percentages are derived from the actual number of receptor-bearing cells.

EXAMPLE

Figure 1:
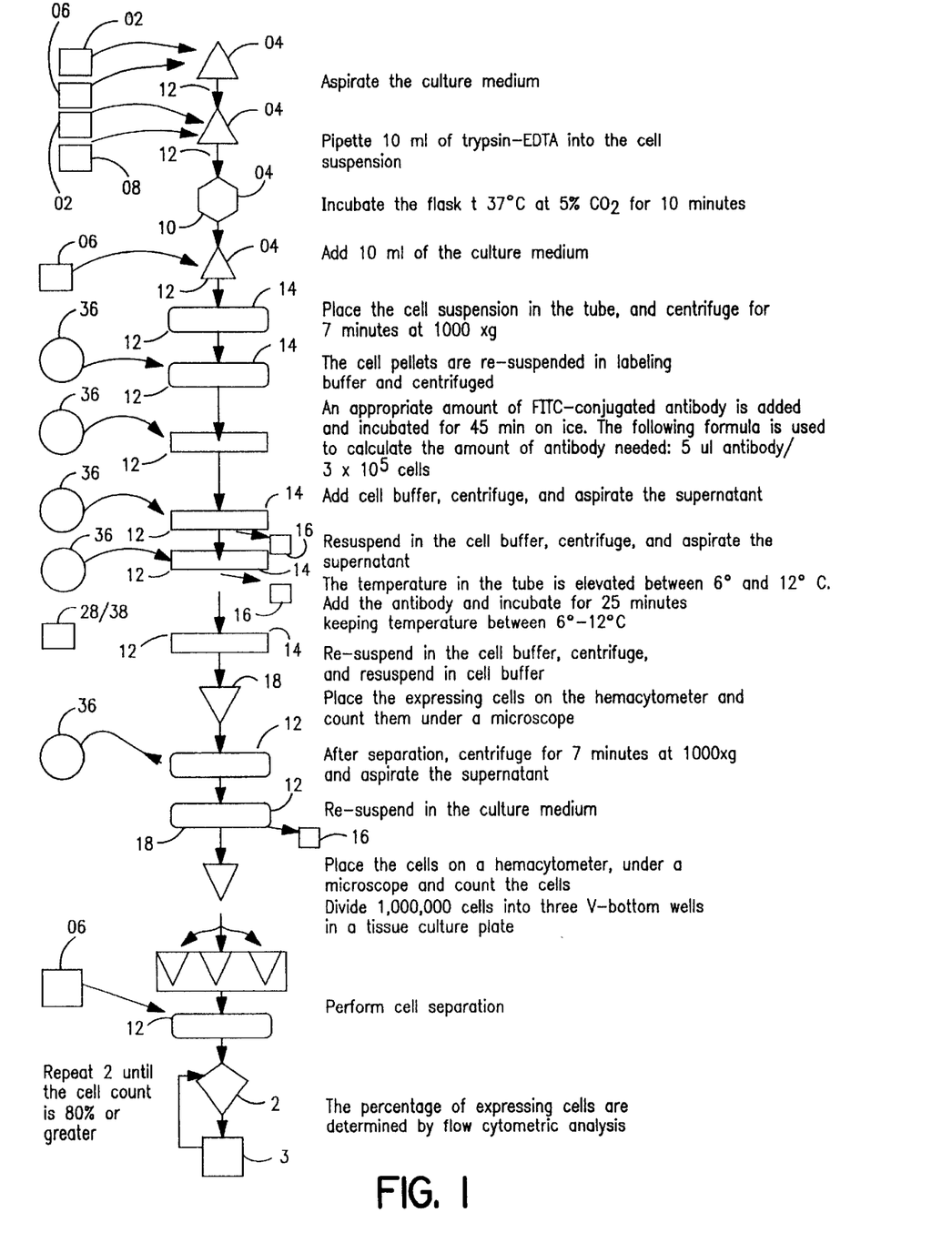
FIG. 1 shows immunomagnetic separation of cells.

This invention utilizes a culture medium 06 of confluently-grown transfected cells 02. The culture medium 06 is removed from the flask 04 by aspiration. Then trypsin-EDTA 08 is pipetted and the cell suspension 12 is incubated in a $CO_2$ incubator 10 min. at 37° C. with 5% $CO_2$. After this, 10 ml of the culture medium 06 is added to the cell suspension 12. The cell suspension 12 is prepared for column 40 separation by placing the cell suspension 12 in the tube 32 and centrifuging. Appropriate FITC-conjugated antibody 30 is added and gently mixed by swirling the tube 32. The mixture is incubated for 45 minutes at 4° C. on ice. The tube 32 is then centrifuged and the supernatant 16 is aspirated. The cell pellets are re-suspended in 1× phosphate buffer solution 46 and centrifuged. The cell suspension 12 is centrifuged and the supernatant 16 is aspirated one more time. The resulting cell pellets are re-suspended in diluted, degassed cell buffer solution 36. The temperature of the tube 32 is maintained at 4° C. on ice and anti-FITC microbeads are added. The tube 32 is incubated for 15 minutes at 4° C. on ice. For optimum anti-FITC antibody magnetic bead conjugation 38, the suspension 12 must be maintained at a temperature of 4° C. The cell suspension is then diluted with additional diluted, de-gassed cell buffer solution 36.

The following procedure is performed twice: The cell suspension 12 is combined with cell buffer solution 36, centrifuged, and then the supernatant 16 is aspirated. The cell pellet is re-suspended in diluted, de-gassed cell buffer solution 36.

Figure 2:
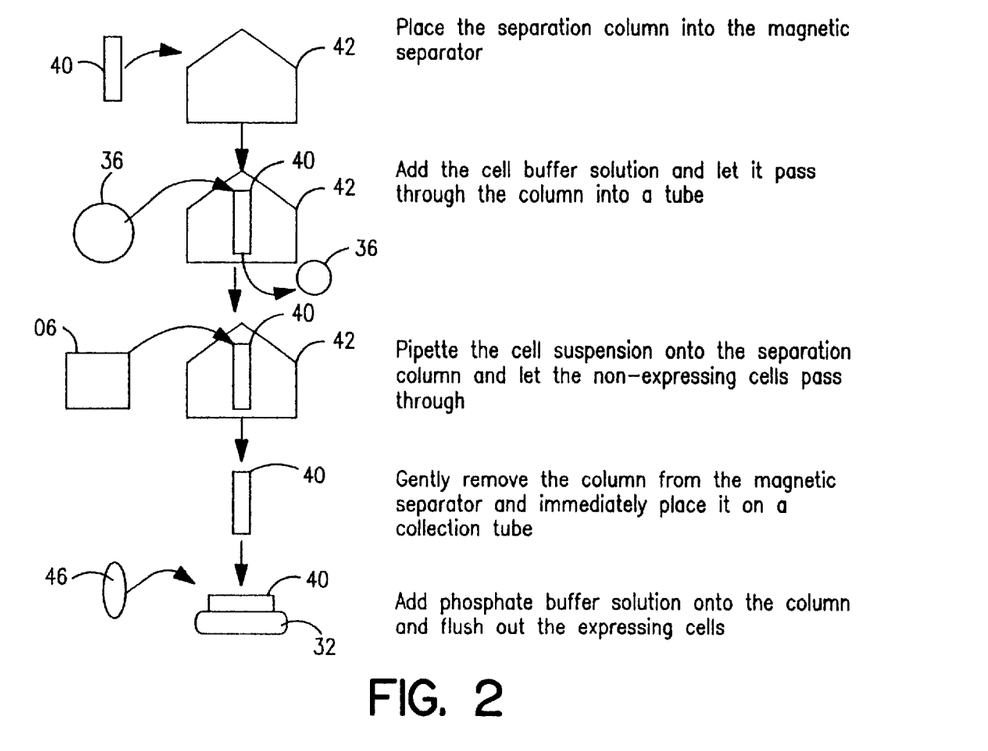
FIG. 2 shows cells being counted on a hemocytometer after being enriched for viral receptors and coreceptors.

To achieve the desired percentage of expressing cells, column separation is performed. The separation column 40 is placed in a magnetic separator 42, the tip removed, and filled with a diluted, de-gassed cell buffer solution 36. The column 40 is equilibrated with the diluted cell buffer solution 36, and is eluted by passing it through the column 40 into a tube 32 and disposing of it appropriately. The cell suspension 12 is then pipetted onto the equilibrated separation column 40, which is held in the magnetic separator 42, and the non-expressing cells are allowed to pass through. The non-expressing cells are collected in the tube 32. The column is then washed three times with the diluted cell buffer solution 36 to collect non-expressing cells. The separation column 40 is removed gently from the magnetic separator 42 and immediately placed on a collection tube 32. Cell buffer solution 36 is pipetted onto the separation column 40. The fraction of the expressing cells is flushed out, using a plunger. Next, an aliquot of cells are placed on a hemacytometer 18, viewed under a microscope 20 and counted, or analyzed by flow cytometry.

Figure 3:
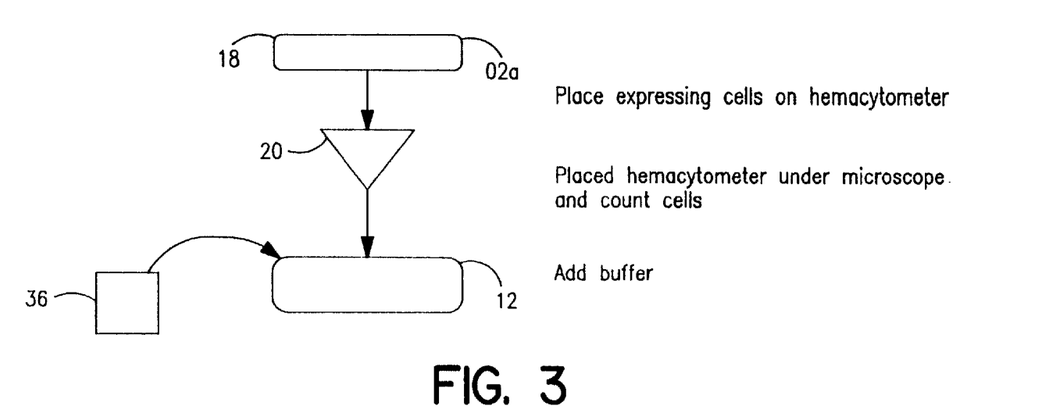
FIG. 3 is a flow chart showing cultured cells being stained with antibody, counted with a hemocytometer, separated, and then the percentage of expressing cells determined by flow cytometric analysis.

The cell suspension 12 is placed in a centrifuge tube 32 and centrifuged for 7 minutes at 1000×g. The cells 02 should form pellets at the bottom of the centrifuge tube 32, whereupon the supernatant 16 is aspirated out of the tube 32. The cell pellets are resuspended in the culture medium 06. One droplet from the cell suspension 12 is removed by a pipette and placed on a hemacytometer 18. The hemacytometer 18 is covered with a slip and placed on a microscope 20 so that the cells 02 can be counted. After the count, one million cells are divided into three wells 22 of a 96-well, V-bottom tissue culture plate 24. The plate 24 is centrifuged at 1400×g for 4 minutes.

After the tissue culture plate 24 has been centrifuged, the supernatant 16 is removed and the labeling buffer 26 is added. The tissue culture plate 24 is centrifuged again, and the supernatant 16 is removed. Antibodies 28 are added to two of the three wells 22 of the tissue culture plate 24, leaving the third one for a control. The add 5 µl of antibodies tot he appropriated wells and incubated for 45 minutes. After incubation, 200 µl of labeling buffer 26 is added. The percentage of positive antigens in the cell suspension 12 is then determined by the analysis of the suspension 12 using flow cytometry. If less than 80% of the cells 02 express both markers, column separation must be performed again until the desired percentage of expressing cells is reached.

The transfected cells 02 which are 80% positive for both markers are counted and plated into a sterile, 24-well, tissue culture plate 24 at a concentration of $4 \times 10^4$ per well 22. The transfected cells 02 are then cultured for 2 days or until they reach 30% to 50% confluence.

Preferred Embodiment—Operation

This invention utilizes a culture medium 06 of confluently grown HeLa-CD4-LRT-β-gal cells 02. The culture medium 06, which can be, e.g., RPMI or DMEM containing 10% fetal calf serum, and, optionally:

100 U/ml penicillin;
100 µg/ml streptomycin;
0.25 µg/ml fungizone; or
300 µg/ml glutamine is removed from the flask 04 by aspiration. Then 5 ml of trypsin-EDTA 08 is pipetted into the cell suspension 12 and the cell suspension 12 is incubated in a $CO_2$ incubator 10 at 37° C. with 5% $CO_2$. After this, 10 ml of the culture medium 06 is pipetted into the cell suspension 12. The cell suspension 12 is prepared for column 40 separation in the following manner.

The cell suspension 12 is placed in the tube 32 and centrifuged 100×g for 6 minutes at 4° C. To the cell suspension 12, 5 microlitres of the appropriate FITC-conjugated anti-HIV antibody 30 is added for every 300,000 cells and gently mixed by swirling the tube 32. The mixture is incubated for 45 minutes at 4° C. on ice. The tube 32 is then centrifuged and the supernatant 16 aspirated. The cell pellets are re-suspended in 1× phosphate buffer solution 46 and centrifuged. The cell suspension 12 is centrifuged again and the supernatant 16 is aspirated. The cell pellets are re-suspended in 2.0 ml of 1× diluted, de-gassed cell buffer solution 36. The cell suspension 12 is centrifuged and the supernatant 16 is aspirated one more time. The resulting cell pellets are re-suspended in 2.0 ml of 1× diluted, de-gassed cell buffer solution 36. The temperature of the tube 32 is elevated to between 6 and 12° C. and maintained at 4° C. on ice and 0.01 ml anti-FITC magnetic bead conjugate 38 added. The tube 32 is incubated for 15 minutes at 4° C. on ice. For optimum anti-FITC antibody magnetic bead 38 conjugation, the suspension 12 must be maintained at a temperature of 4° C. in a refrigerator. The cell suspension 12 is then diluted with an additional 0.4 ml of diluted, de-gassed cell buffer solution 36.

The following procedure is performed twice. The cell suspension 12 is combined with 2 ml of cell buffer solution 36, centrifuged, and the supernatant 16 is aspirated. The cell pellet is re-suspended in 1 ml of diluted, de-gassed cell buffer solution 36.

To achieve the desired percentage of expressing cells, column 40 separation is performed in the following manner. The separation column 40 is placed in a magnetic separator 42, the tip removed, and filled with 0.5 ml of a diluted, de-gassed cell buffer solution 36. The diluted cell buffer solution 36 is eluted by passing it through the column 40 into a 12×75 mm culture tube 32 and disposing of it appropriately. The cell suspension 12 is then pipetted onto the separation column 40, which is contained in the magnetic separator 42, and the non-expressing cells are allowed to pass through. The non-expressing cells are collected in the 12×75 mm culture tube 32. The column 40 is then washed six times with 0.5 ml of the diluted cell buffer solution 36 to collect non-expressing cells. The separation column 40 is removed gently form the magnetic separator 42. It is immediately placed on a 12×75 mm culture tube 32 and 3 ml of cell buffer solution 36 is pipetted onto the separation column 40. The fraction of the expressing cells is flushed out, using a plunger, leaving 2 ml in the column reservoir. An aliquot of cells is placed on a hemacytometer 18, viewed under a microscope 20 and counted, or analyzed by flow cytometry.

The cell suspension 12 is placed in a 15 ml centrifuge tube 32 and centrifuged for 7 minutes at 1000×g. The cells should form pellets at the bottom of the centrifuge tube 32, whereupon the supernatant 16 is aspirated out of the tube 32. The cell pellets are resuspended in 10 ml of the culture medium 06. One droplet from the cell suspension 12 is removed by a Pasteur pipette, placed on a hemacytometer 18, and covered with a slip. The hemacytometer 18 is then placed on a microscope 20 so that the cells 02 can be counted. After the count, one million cells are divided into three wells 22 of a 96-well, V-bottom tissue culture plate 24 using a Pasteur pipette. The tissue culture plate 24 is centrifuged at 1400×g for 4 minutes.

After the tissue culture plate 24 has been centrifuged, the supernatant 16 is removed. The tissue culture plate 24 is centrifuged again, and the supernatant 16 removed. Then, using a pipette, 5 µl of antibodies 28 are added to two of the three wells 22 of the tissue culture plate 24, leaving the third one for a control, and incubated for 45 minutes. Again, 5 µl of antibodies 28 are added to the appropriate wells 22 and the plate 24 is incubated for 45 minutes. After incubation, 200 µl of the labeling buffer 26 is added. The labeling buffer 26 consists of:

1× phosphate buffer solution 46
1.0% bovine serum albunim
0.1% sodium azide

The percentage of positive antigens in the cell suspension 12 is then determined by the analysis of the suspension 12 using flow cytometry. If less than 80% of the cells 02 express both markers, column 40 separation, as described above, must be performed again until the desired percentage of expressing cells 02 is reached.

The transfected cells 02 which are 80% positive for both markers are counted and plated with a pipette in a sterile, 24-well 22 tissue culture plate 24 at a concentration of $4 \times 10^4$ per well 22. The transfected cells 02 are then cultured for 2 days or until they reach 30% to 50% confluence.

Conclusions and Ramifications

Accordingly, it can be seen that the present invention would allow for transfected cells to be immunomagnetically separated to improve the receptivity of such cells.

Although the description above contains many specifics, these should not be construed as limiting the scope of the invention but as merely providing illustrations of some of the presently preferred embodiments of this invention. Various other embodiments and ramifications are possible within its scope. A cell line, genetically engineered to express a special receptor or specific receptors as a result of transfection, is provided. The invention method utilizes the genetically-engineered cell HeLa-CD4-LTR-β-gal. In addition, a method of immunomagnetic separation, that utilizes a genetically-engineered antibody designed to attach to the indicated receptor or receptors, and a genetically-engineered antibody or antibodies is provided. This antibody or antibodies may be an HIV-polyclonal antibody.

The method of preparing cells for immunomagnetic separation is comprised of the following steps. Trypsin is added into the culture medium and the cells suspension is incubated in a $CO_2$ incubator at 37° C. with 5% $CO_2$. To this suspension, 10 ml of the culture medium is added. The cell suspension is prepared for column separation by placing the cell suspension in a tube and centrifuged. Then, 0.085 ml of a fluorochrome-conjugated anti-HIV polyclonal antibody or an appropriate amount of monoclonal antibody is added and mixed by gently swirling the tube. The mixture is incubated for 45 minutes at 4° C. on ice. The tube is centrifuged and the supernatant is aspirated. The resulting cell pellets are re-suspended in 2 ml of 0.5% 1× phosphate buffer solution and incubated for 30 minutes at 4° C. on ice in the dark. The cell suspension is again centrifuged and the supernatant is aspirated. The cell pellets are re-suspended in 1.5 ml diluted, de-gassed cell buffer solution, and the cell suspension is again centrifuged and the supernatant is aspirated one more time. The resulting cell pellets are re-suspended in 0.09 ml diluted, de-gassed cell buffer solution. The temperature of the tube is elevated to between 6° C. and 12° C. and antibody, or anti-fluorochrome antibody magnetic bead conjugate is added. The antibody may be conjugated to FITC, and paramagnetic microbeads may be conjugated to anti-FITC. In addition, the antibody may be conjugated to phycoerythrin and paramagnetic-conjugated anti-phycoerythrin (any fluorochrome is suitable). The tube is incubated for 15 minutes between 6° C. and 12° C. The cell suspension is combined with 2 ml anti-FITC magnetic bead conjugate and the suspension is centrifuged, the supernatant is aspirated, the cell pellet re-suspended in 1 ml diluted, de-gassed cell buffer solution, and this procedure is repeated again.

The cells are next added to a culture medium comprising RPMI 1640 and DMEM containing 10% fetal calf serum and, optionally, antibiotics, antifungal agents, amino acids, etc. Immunomagnetic separation is performed as follows. The separation column is placed in a magnetic separator and the column is filled with a 5 ml diluted, de-gassed cell buffer solution. The column is eluted of the diluted cell buffer solution by passing it through the column into a 10 ml tube and disposing of it properly. The cell suspension is then pipetted onto the separation column, which is contained in the magnetic separator. The non-expressing cells are allowed to pass through, and are collected in the tube. The column is washed three times with 1.0 ml of the diluted cell buffer solution. The separation column is removed fro the magnetic separator and immediately placed on a 10 ml collection tube. Next, 3 ml of 1× phosphate buffer solution is pipetted onto the separation column. The fraction of the expressing cells is flushed out, using a plunger.

The expressing cells are counted by placing them on a hemacytometer, viewing them under a microscope, and counting them; they may also be analyzed using flow cytometry.

The cell suspension is tested by dividing one million cells into three wells of a 96-well, V-bottom tissue culture plate. The plate is centrifuged at 1400×g for 4 minutes. The supernatant is removed, the plate is centrifuged and the supernatant is removed again. Antibodies are added to two of the three wells of the tissue culture plate, leaving the third one for a control, and the plate is incubated for 45 minutes. Then 200 μl of labeling buffer, which consists of 10× phosphate buffer solution, 1.0% bovine serum albumin, and 0.1% sodium azide, is added. The percentage of positive antigens in the cell suspension may be determined using flow cytometry, so that 80% of the transfected cells express both markers. The transfected cells are counted and plated in a sterile, 24-well tissue culture plate at a concentration of $4 \times 10^4$ per well. The transfected cells are cultured for 2 days in a 5% $CO_2$ atmosphere at 37° C. or until they reach 30% to 50% confluence.

| List of Reference Numerals | |
|---|---|
| 02 | Transfected Cells |
| 04 | Flask |
| 06 | Culture Medium |
| 08 | Trypsin-EDTA |
| 10 | $CO_2$ Incubator |
| 12 | Cell Suspension |
| 14 | Centrifuge Tube |
| 16 | Supernatant |
| 18 | Hemacytometer |
| 20 | Microscope |
| 22 | Well |
| 24 | Tissue Culture Plate |
| 26 | Labeling Buffer |
| 28 | Antibodies |
| 30 | Polyclonal Antibody Reagent |
| 32 | Tube |
| 34 | Paraformaldehyde |
| 36 | Cell Buffer Solution |
| 38 | Magnetic Bead Conjugate |
| 40 | Column |
| 42 | Magnetic Separator |
| 44 | Column Preservative |
| 46 | Phosphate Buffer Solution |

Thus the scope of the invention should be determined by the appended claims and their legal equivalents, rather than by the examples given.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures, including U.S. Provisional Application Ser. No. 60/083,078, filed Apr. 27, 1998, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of improving the HIV receptivity of a continuous cell line transformed with DNAs coding for expressible CD4 and expressible HIV-1 coreceptor in an assay for HIV-1, comprising:

a) positively-selecting cells which co-express CD4 and HIV-1 coreceptor on their cell surface, thereby improving their HIV receptivity in comparison to cells not positively-selected, wherein said cells have been transformed with DNAs coding for expressible CD4 and expressible HIV-1 coreceptor;
   b) contacting said positively-selected cells with HIV-1 under conditions effective for said HIV-1 to infect said cells; and
   c) detecting the number of cells infected with HIV-1, thereby assaying for infectivity of HIV-1.

2. A method of claim 1, wherein said continuous cell line is a human cell line.

3. A method of claim 2, wherein said human cell line is a HeLa cell line.

4. A method of claim 3, wherein said HeLa cell line is MAGI-CCR5.

5. A method of claim 1, wherein positively-selecting comprises:
   a) labeling said cells transformed with DNAs coding for expressible CD4 and expressible HIV-1 coreceptor with a CD4 binding reagent;
   b) separating out CD4 binding reagent labeled cells;
   c) labeling said cells from b) with a HIV coreceptor binding reagent; and
   d) separating out HIV-1 coreceptor binding reagent labeled cells from c).

6. A method of claim 5, wherein separating is by positive selection using immunomagnetic separation or fluorescence-activated cell sorting.

7. A method of claim 5, wherein said binding reagents are antibodies conjugated to a capture-moiety.

8. A method of claim 5, wherein said CD4 binding reagent is a FITC-conjugated CD4-specific antibody.

9. A method of claim 5, wherein said HIV-1 coreceptor binding reagent is a FITC-conjugated HIV-1-coreceptor specific antibody.

10. A method of claim 5, wherein said HIV-1 coreceptor is CCR5.

11. A method of claim 5, wherein:
    said (a) labeling comprises:
        contacting said cells with a CD4 binding reagent which is FITC-conjugated CD4-specific antibody under conditions effective for antibody to label cell-surface CD4; and
    said (b) separating out comprises:
        contacting cell-surface labeled cells with anti-FITC antibody magnetic particles under conditions effective for said antibody to attach to said CD4-specific antibody on said cell-surface;
        applying a magnetic field to said labeled cells which is effective to retain said magnetic particles; and
        eluting the retained particles to form a sample of separated out cells.

12. A method of claim 5, wherein:
    said (c) labeling comprises:
        contacting said cells with a HIV-1 coreceptor binding reagent which is FITC-conjugated HIV-1 coreceptor-specific antibody under conditions effective for antibody to label cell-surface HIV-1 coreceptor; and
    said (d) separating out comprises:
        contacting cell-surface labeled cells with anti-FITC antibody magnetic particles under conditions effective for said antibody to attach to said HIV-1 coreceptor-specific antibody on said cell-surface;
        applying a magnetic field to said labeled cells which is effective to retain said magnetic particles; and
        eluting the retained particles to form a sample of separated out cells.

13. A method of claim 12, wherein said HIV-1 coreceptor is CCR5.

14. A method of claim 5, wherein said continuous cell line is a human cell line.

15. A method of claim 5, wherein said human cell line is a HeLa cell line.

16. A method of claim 5, wherein said HeLa cell line is MAGI-CCR5.

17. A method of claim 1, wherein said cells are cultured for 2 days prior to (c) detecting.

18. A method of assaying for the infectivity of HIV-1 in a continuous cell line transformed with DNAs coding for expressible CD4 and expressible HIV-1 coreceptor, comprising:
    a) contacting said positively-selected cells with HIV-1 under conditions effective for said HIV-1 to infect said cells;
    b) detecting the number of cells infected with HIV-1, thereby assaying for infectivity of HIV-1; and
    c) wherein said positively-selected cells have been positively selected for co-expression of CD4 and HIV-1 coreceptor on their cells receptivity surface, thereby improving their HIV receptivity in comparison to cells which have not been positively-selected, and wherein said cells have been transformed with DNAs coding for expressible CD4 and expressible HIV-1 coreceptor.

* * * * *